United States Patent
Specht et al.

(10) Patent No.: US 8,594,808 B2
(45) Date of Patent: Nov. 26, 2013

(54) STIMULATION ELECTRODE

(75) Inventors: Heiko Specht, Hanau (DE); Frank Krüger, Nidderau (DE); Ulrich Hausch, Frankfurt (DE); Andreas Reisinger, Malterdingen (DE)

(73) Assignee: W. C. Heraeus GmbH, Hanau (DE)

( * ) Notice: Subject to any disclaimer, the term of this patent is extended or adjusted under 35 U.S.C. 154(b) by 344 days.

(21) Appl. No.: 12/790,270

(22) Filed: May 28, 2010

(65) Prior Publication Data
US 2010/0305671 A1    Dec. 2, 2010

(30) Foreign Application Priority Data
May 29, 2009    (DE) .......................... 10 2009 023 163

(51) Int. Cl.
*A61N 1/00*    (2006.01)
(52) U.S. Cl.
USPC .......................................... 607/121; 607/116
(58) Field of Classification Search
USPC ................................................ 607/115–128
See application file for complete search history.

(56) References Cited

U.S. PATENT DOCUMENTS

| | | | |
|---|---|---|---|
| 4,082,900 A * | 4/1978 | Shimogori et al. | 428/336 |
| 4,717,581 A * | 1/1988 | Robblee | 427/2.12 |
| 7,801,623 B2 * | 9/2010 | McVenes et al. | 607/116 |
| 2007/0265692 A1 | 11/2007 | Koop et al. | |

FOREIGN PATENT DOCUMENTS

| | | |
|---|---|---|
| DE | 69824312 | 6/2005 |
| WO | 2006104432 | 5/2006 |

* cited by examiner

*Primary Examiner* — Scott Getzow
(74) *Attorney, Agent, or Firm* — Dicke, Billig & Czaja, PLLC

(57) ABSTRACT

One aspect relates to a stimulation electrode including an electrically conducting base body. The base body encompasses tantalum and is at least partially covered with a porous tantalum oxide layer, which is anodically applied by means of high voltage pulses. Provision is made according to an embodiment for a metallic protective layer to cover the porous tantalum oxide layer so as to prevent a hydrogen embrittlement.

8 Claims, 3 Drawing Sheets

STIMULATION ELECTRODE

CROSS-REFERENCE TO RELATED APPLICATIONS

This Utility Patent Application claims priority to German Patent Application No. DE 10 2009 023 163.3, filed on May 29, 2009, which is incorporated herein by reference.

BACKGROUND

One aspect relates to a stimulation electrode. Published Application WO 2006/104432 A1 describes an implantable stimulation electrode. This electrode encompasses a base body of niobium. A porous niobium oxide layer is applied onto the base body by means of a described high voltage pulse method. Stimulation electrodes, which are embodied in such a manner, can be used, for example, for stimulating a heart by means of a pace maker or as neural stimulation electrode. Electric pulses are thereby transferred to the heart via the stimulation electrode. The porous niobium oxide layer, however, becomes very brittle within the human body. Particles of the porous niobium oxide layer can thus detach, which in turn can lead to an interference of the stimulation electrode or, in the worst case, to a danger to the patient.

An implantable stimulation electrode, which encompasses a porous layer on a base body, is also described in Published Application US 2007/0265692 A1. Patent Specification DE 698 24 312 T2 describes a tantalum wire, which is provided with a protective layer in a multi-step process.

For these and other reasons, there is a need for the present invention, providing a stimulation electrode with good biocompatibility and good contact characteristics with a simultaneously low risk to the patient.

SUMMARY

One aspect relates to a stimulation electrode with an electrically conducting base body, and in one embodiment, the base body encompasses tantalum and the base body is at least partially covered by a porous tantalum oxide layer, which is anodically applied by means of high voltage pulses.

One aspect furthermore relates to a method for producing a stimulation electrode with an electrically conducting base body, which encompasses tantalum and onto which a porous tantalum oxide layer is at least partially applied by means of high voltage pulses.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
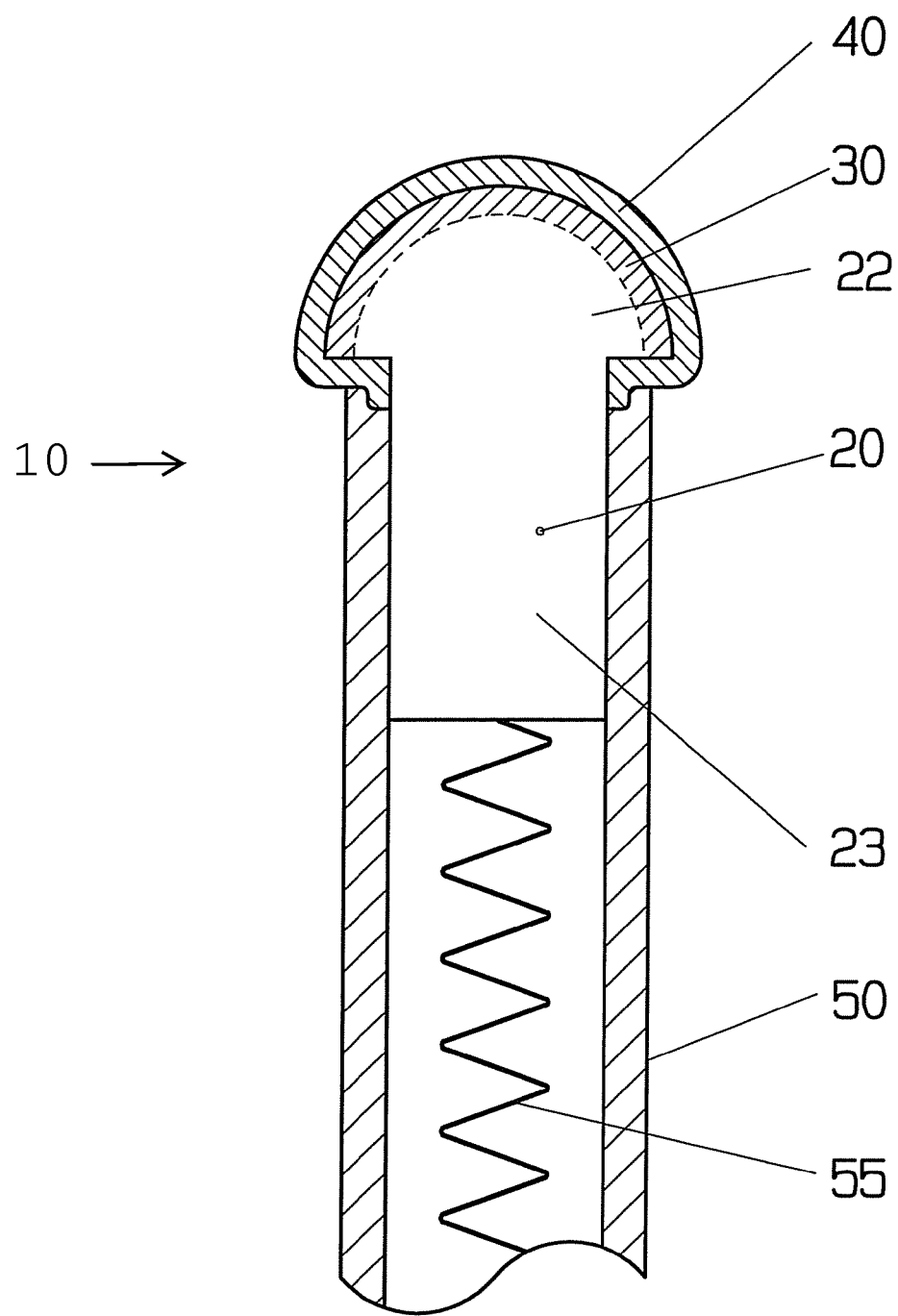
FIG. 1 illustrates a schematic sectional view through a distal end of a stimulation electrode of an electrode feed line according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment is a stimulation electrode and method of producing a stimulation electrode. The stimulation electrode according to one embodiment is characterized in that a metallic protective layer covers the porous tantalum oxide layer so as to prevent a hydrogen embrittlement.

One aspect thereby lies in that the metallic protective layer prevents a diffusion of the hydrogen into the porous tantalum oxide layer. The metallic protective layer consequently seals the porous tantalum oxide layer from being affected by the environment. An embrittlement of the tantalum oxide layer is thus prevented, so that it remains flexible enough to prevent a chipping of individual areas. Depending on the chosen material for the metallic protective layer, the flexibility of the stimulation electrode—also referred to as electrode hereinbelow—can furthermore also remain protected for longer periods of time.

The metallic protective layer according to one embodiment furthermore provides that the capacitance of the stimulation electrode, as compared to that from the state of the art, is increased in response to virtually the same geometric surface, whereby the impedance is reduced accordingly. This ensures a reliable contact between the electrode and an organ of the patient. The danger of an interference of the function of the electrode by the metallic protective layer is also reduced. The stimulation electrode according to one embodiment thus combines the positive effect of the porous tantalum oxide layer, which is generated by means of the high voltage pulses, with the safety of a metallic protective layer. The large surface of the porous tantalum oxide layer provides for an improved growth of the implant into the tissue. This feature is supplemented by the metallic protective layer, which prevents a hydrogen embrittlement—also referred to as embrittlement hereinbelow—of the porous tantalum oxide layer.

The base body of the stimulation electrode according to one embodiment encompasses the valve metal tantalum or consists thereof. A base body, which is embodied in such a manner, is provided with a tantalum oxide layer by means of high voltage pulses. The method used for this is also referred to as plasma-electrolytic oxidation (PEO) and is described in more detail in WO 2006/104432 A1 for niobium. In the disclosed method, a porous structure of the corresponding metal oxide is generated on the surface of the base body by means of plasma-electrolytic oxidation. It thereby turned out to be an anomaly that the porous structure encompasses pores, which are considerably larger than it is known from the current state of the art. In the context of the embodiment disclosed herein, a thin, fractal layer of an inert metal is subsequently applied onto this porous structure as a metallic protective layer, whereby a further increase of the surface as well as of the electric conductivity are attained.

The terms "encompassing tantalum" and/or "the tantalum oxide layer" are to clarify that the base body and/or the tantalum oxide layer at least partially consist of tantalum. The base body as well as the tantalum oxide layer can also completely consist of tantalum or of a tantalum-containing alloy. In one embodiment, the base body and/or the tantalum oxide layer encompasses a tantalum-niobium-tungsten alloy (TaNbW alloy comprising 10 weight % of niobium and 7.5 weight % of tungsten) or consists thereof. The tantalum-niobium-tungsten alloy turned out to be preferred as base material for the base body and the tantalum oxide layer, because its tensile strength is almost twice as high and because its specific capacitance is almost twice as high as compared to that of the often used platinum-iridium-10 alloy (PtIr10). A reduction of the losses in response to the transfer of stimulation pulses is thus possible.

It turned out to be advantageous when the stimulation electrode encompasses a tantalum oxide layer, which encompasses an inner closed first oxide layer and an outer porous second oxide layer. In this embodiment alternative, the tantalum oxide layer is consequently designed in two parts. On the one hand, the inner closed first oxide layer, which ensures that the base body is enclosed by a constant, uninterrupted oxide layer. The second oxide layer connects to the first oxide layer radially away from the center axis of the base body. This second oxide layer encompasses the pores, which are provided for an increase of the surface of the stimulation electrode. The first oxide layer prevents the pores of the second oxide layer from reaching up to the base body and said base body is thus partially equipped without an oxide layer. There is thus no direct contact between the metallic protective layer and the base body in the area of the tantalum oxide layer.

It turned out to be advantageous when the metallic protective layer consists of a member of the group of the platinum metals. In the case of extensive measurements, it turned out that it is advantageous when the metallic protective layer encompasses at least one from the following group: platinum, iridium or iridium oxide or an alloy, which encompasses one of the three mentioned metals. The use of platinum lends itself, because this metal is flexible and thus guarantees the flexibility of the stimulation electrode according to one embodiment. A metallic protective layer of platinum can furthermore be applied evenly, thin, yet permanently consistent onto the tantalum oxide layer. A metallic protective layer, which encompasses iridium, also turned out to be advantageous, because it has a good biocompatibility.

A further embodiment of the stimulation electrode is characterized in that the metallic protective layer encompasses a layer thickness of between 0.01 µm to 10 µm, in particular of between 0.5 µm to 5 µm, in particular of between 0.1 µm to 1 µm. In the context of extensive measurements, it turned out that the mentioned layer thicknesses on the one hand effectively prevent a hydrogen embrittlement of the tantalum oxide layer. On the other hand, protective layers of this thickness increase the capacitance of the stimulation electrode according to one embodiment to a degree, which is advantageous for the use in biomedicine. A metallic layer thickness of between 2 µm and 4 µm turned out to be advantageous, in particular in response to the use of a tantalum-niobium-tungsten alloy (tantalum comprising 10 weight % of niobium and 7.5 weight % of tungsten). The required quantity of the metal is thereby small and the desired effects were still attained to a sufficient degree. In the context of measurements, it was possible to prove that a simulated use in a human body was possible for several years with a metallic protective layer of platinum comprising an average layer thickness of 0.5 µm, without the appearance of a hydrogen embrittlement of the porous tantalum oxide layer.

A further embodiment alternative is characterized in that the porous tantalum oxide layer encompasses a pore size of between 0.5 µm to 25 µm, in particular of between 2 µm to 15 µm, in particular of between 3 µm to 10 µm. The longest reach within a pore of the porous tantalum oxide layer is thereby referred to as pore size. It is furthermore advantageous when the porous tantalum oxide layer encompasses a layer thickness of between 1 µm to 20 µm, in particular of between 2 µm to 15 µm, in particular of between 3 µm to 10 µm. The described variables encompass a good ratio between contact surface to overall surface of the electrode.

The capacitance of the stimulation electrode is increased by applying the metallic protective layer onto the porous tantalum oxide layer. It turned out to be advantageous when the stimulation electrode and/or the porous tantalum oxide layer in combination with the metallic protective layer encompass an electric capacitance of at least 5 mF/cm$^2$. The capacitance of at least 5 mF/cm$^2$ is to thereby be reached in a physiological sodium chloride solution (0.9% NaCl in deionized water) at a temperature of 37° C. and a measuring frequency of 100 mHz. A capacitance, which encompasses at least the mentioned magnitude, provides for a reliable transfer of pulses into the tissue of the patient or a reliable detection of pulses from the tissue.

The use of a metallic, in particular platinum-containing protective layer is also disclosed in the context of the embodiments for covering a porous tantalum oxide layer, which is anodically applied by means of high voltage pulses, onto a tantalum-containing base body of a stimulation electrode, for preventing a hydrogen embrittlement. Details and features, which are thereby disclosed in combination with the stimulation electrode or the method for producing the stimulation electrode also apply in combination with the use of the metallic protective layer.

One embodiment furthermore relates to a method for producing a stimulation electrode comprising an electrically conductive base body, which encompasses tantalum and on which a porous tantalum oxide layer is at least partially applied by means of high voltage pulses. Provision is hereby made according to one embodiment for a metallic protective layer to be applied onto the porous tantalum oxide layer, so as to prevent a hydrogen embrittlement of the porous tantalum oxide layer.

It goes without saying that features and details, which are described in combination with the stimulation electrode according to the embodiments, thereby also apply in combination with the method. A method according to one embodiment protects the porous tantalum oxide layer by means of the metallic protective layer. A hydrogen embrittlement of the porous tantalum oxide layer is prevented by means of the metallic protective layer. The hydrogen from the tissue cannot permeate into the porous tantalum oxide layer and cause an embrittlement there. It thereby turned out to be advantageous when the metallic protective layer is used up by means of at least one of the following methods: sputtering, spraying or evaporation.

FIG. 1 illustrates a stimulation electrode 10 according to one embodiment as a part of an electrode system. The stimulation electrode 10 encompasses a front end 22, which is embodied in the illustrated embodiment alternative in a mushroom-like manner. This embodiment is to be understood only as an exemplary possible form of the stimulation electrode 10, because it can also encompass any other form, such as, for example, a ring-shaped, coil-shaped or flat embodiment. A rear end 23, which is embodied in a cylinder-shaped manner, connects to the front end 22, which is embodied in a mushroom-like manner. This rear end 23 is connected to a wire 55. This wire 55 can be connected to a pace maker, for example, which is not illustrated herein. A sealing silicon tube 50 is pushed over the wire 55 as well as parts of the rear end 23 of the stimulation electrode 10. This silicon tube 50 prevents environmental impacts to have an impact on the wire 55 or parts of the stimulation electrode 10, respectively, and serves the purpose of an electric insulation.

Figure 2:
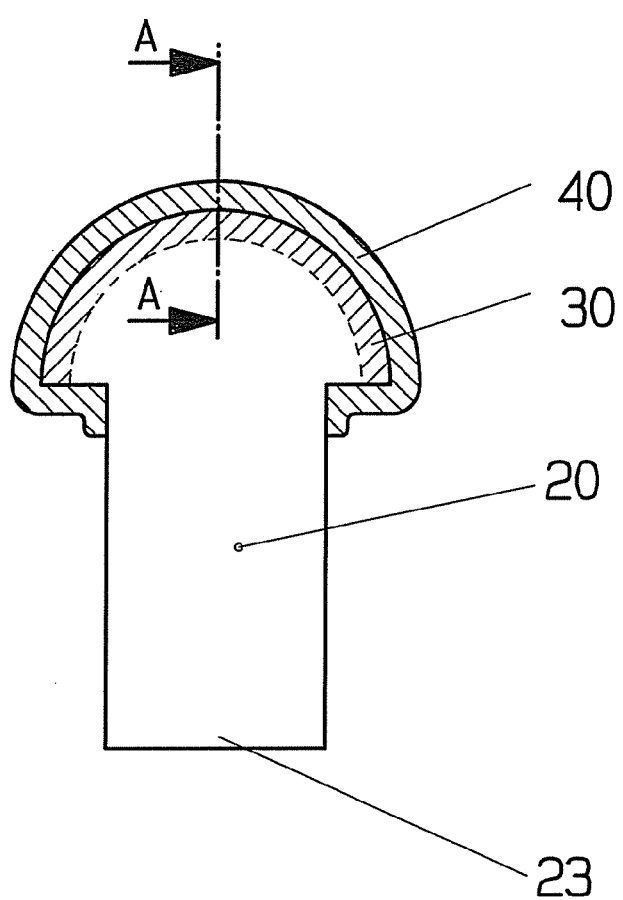
FIG. 2 illustrates a further schematic illustration of the stimulation electrode according to one embodiment.

The stimulation electrode 10 is illustrated in FIG. 2 in a sole position. The stimulation electrode 10 encompasses a base body 20. In the illustrated embodiment alternative, this base body 20 contains tantalum. It turned out to be preferred when the base body 20 consists of a tantalum alloy, which, in addition to tantalum, also encompasses 10 weight % of niobium and 7.5 weight % of tungsten. A porous tantalum oxide layer 30 is applied onto the base body 20 by means of high voltage pulses. The method for applying the porous tantalum oxide layer 30 is described in detail in Published Application WO 2006/104432 A1, so that reference is made to this Published Application and the features thereof with regard thereto.

It became apparent in tests that the above-mentioned tantalum alloy forms particularly even tantalum oxide layers on the surface of the base body. However, the porous tantalum oxide layer 30 is susceptible to a hydrogen embrittlement. To prevent this hydrogen embrittlement, provision is made according to one embodiment for the porous tantalum oxide layer 30 to be surrounded by a metallic protective layer 40. In the illustrated exemplary embodiment, the porous tantalum oxide layer 30 not only covers the front end 22 of the base body 20, but also areas of the rear end 23 of the base body 20, which is embodied in a cylindrical manner. The porous tantalum oxide layer 30 can, but must not, completely cover the base body 20. The porous tantalum oxide layer 30 is covered by the metallic protective layer 40. Said protective layer 40 encompasses a variable, which corresponds to at least that variable of the porous tantalum oxide layer 30, so that a hydrogen embrittlement cannot take place thereon. Consequently, not only the front end 23, but also a larger area of the rear end 23 of the base body 20 is covered with the metallic protective layer 40 in the illustrated exemplary embodiment.

As is also clarified in FIG. 1, the metallic protective layer 40 is applied so far on the rear end 23 of the base body 20 that the silicon tube 50 also covers parts of this metallic protective layer 40. It is thus ensured that a direct contact between the base body 20 and the surrounding tissue does not take place.

Figure 3:
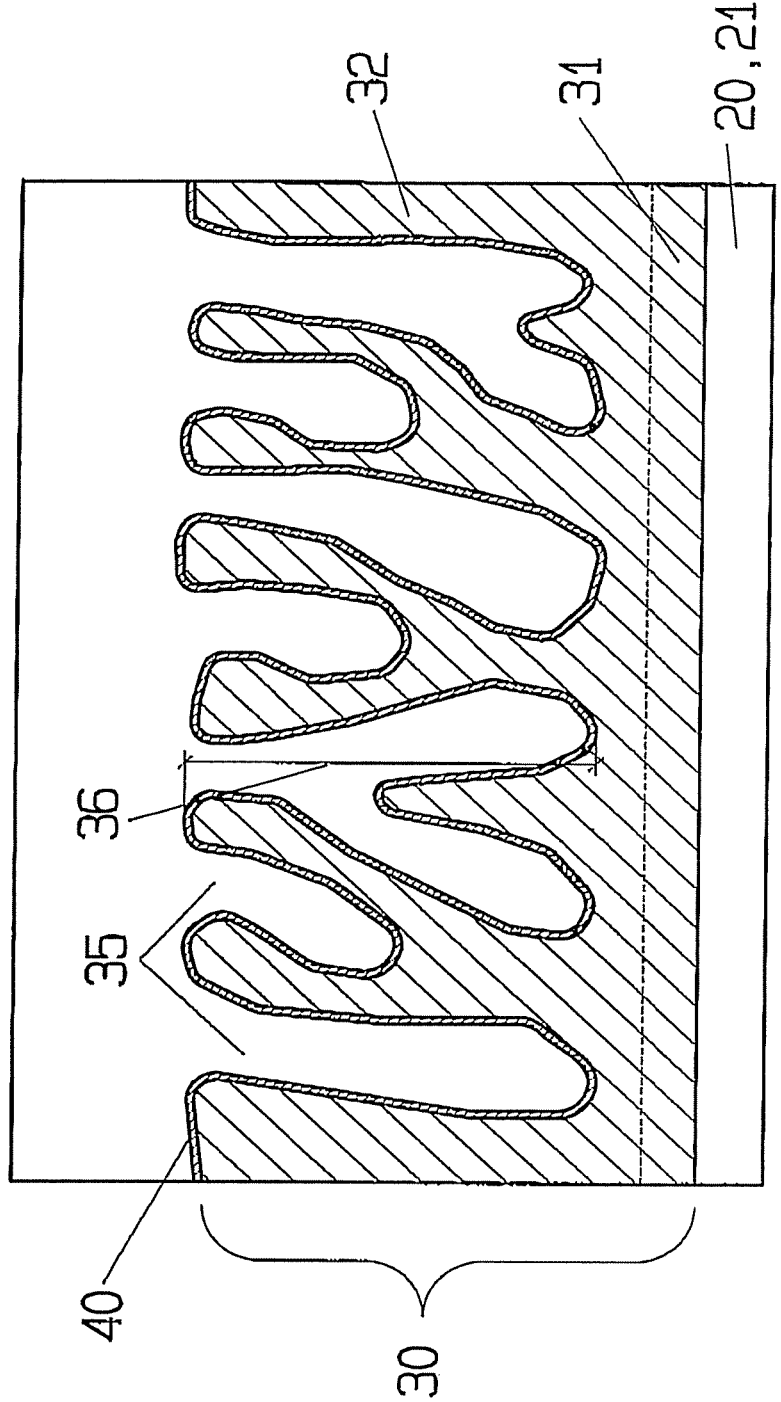
FIG. 3 illustrates a schematic enlargement of the stimulation electrode in the area of the surface.

FIG. 3 illustrates a sectional enlargement of the surface of the stimulation electrode 10 according to one embodiment along sectional line A-A from FIG. 2. A porous tantalum oxide layer 30 is anodically applied onto a tantalum-containing base material 21 of the base body 20 by means of high voltage pulses. It thereby turned out to be advantageous when the porous tantalum oxide layer 30 encompasses an inner closed first oxide layer 31 and an outer porous second oxide layer 32. As is clarified in FIG. 3, the outer porous oxide layer 32 encompasses pores 35, which partially encompass a pore depth 36, which corresponds to the thickness of the second porous oxide layer 32. To prevent the pores 35 of the second oxide layer 32 to project downwardly onto the base material 21, provision is made for the first oxide layer 31. Said first oxide layer forms a protective film above the base material 21 of the base body 20.

To prevent a hydrogen embrittlement, a metallic protective layer 40 is applied onto the tantalum oxide layer 30. In the context of this application, the term "hydrogen embrittlement" refers to the change of the ductility of metals by the permeation and the placement of hydrogen into the metal grid thereof. The hydrogen embrittlement can lead to a hydrogen-induced tear formation. To avoid this, it turned out to be advantageous to apply the metallic protective layer 40 from one of the elements of the platinum group onto the stimulation electrode 10 and/or the porous tantalum oxide layer 30. As is illustrated, the thickness of the metallic protective layer 40 is smaller than the thickness of the porous tantalum oxide layer 30. This prevents a clogging and/or filling of the pores 35, without there furthermore being the danger that the porous tantalum oxide layer 30 is embrittled by the hydrogen of the surrounding tissue. The metallic protective layer 40 furthermore increases the electric capacitance of the stimulation electrode 10. It turned out to be advantageous when the stimulation electrode 10 and/or the porous tantalum oxide layer 30 in connection with the metallic protective layer 40 encompasses an electric capacitance of at least 0.5 mF. The capacitance of at least 5 $mF/cm^2$ is to thereby be reached in a physiological sodium chloride solution (0.9% NaCl in deionized water) at a temperature of 37° C. and a measuring frequency of 100 mHz.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A stimulation electrode comprising an electrically conducting base body, wherein the base body encompasses tantalum and the base body is at least partially covered with a porous tantalum oxide layer, which is anodically applied by means of high voltage pulses, characterized in that a metallic protective layer covers the porous tantalum oxide layer so as to prevent a hydrogen embrittlement and such that the metallic protective layer is an outer layer of the base body adjacent tissue in which the electrode is implanted;

characterized in that the metallic protective layer encompasses at least one from the following group: platinum, iridium or iridium oxide;

characterized in that the tantalum oxide layer encompasses an inner closed first oxide layer and an outer porous second oxide layer;

characterized in that the metallic protective layer encompasses a layer thickness of between 0.01 μm to 10 μm;

characterized in that the porous tantalum oxide layer encompasses a pore size of between 0.5 μm to 25 μm; and characterized in that the stimulation electrode and/or the porous tantalum oxide layer in combination with the metallic protective layer encompasses an electric capacitance of at least 5 $mF/cm^2$.

2. The stimulation electrode according to claim 1, characterized in that the porous tantalum oxide layer encompasses a layer thickness of between 1 μm to 20 m, in particular of between 2 μm to 15 μm, in particular of between 3 μm to 10 μm.

3. A stimulation electrode comprising:
an electrically conducting base body consisting of tantalum;
a porous tantalum oxide layer configured to be anodically applied to the base body by means of high voltage pulses; and
a metallic protective layer covering the porous tantalum oxide layer so as to prevent a hydrogen embrittlement and such that the metallic protective layer is an outer layer of the base body adjacent tissue in which the electrode is implanted;
wherein the tantalum oxide layer comprises an inner closed first oxide layer and an outer porous second oxide layer;
wherein the metallic protective layer comprises a layer thickness of between 0.01 μm to 10 μm; and
wherein the stimulation electrode and/or the porous tantalum oxide layer in combination with the metallic protective layer comprises an electric capacitance of at least 5 mF/cm$^2$.

4. The stimulation electrode according to claim 3, wherein the metallic protective layer comprises at least one from the group: platinum, iridium and iridium oxide.

5. The stimulation electrode according to claim 3, wherein the porous tantalum oxide layer comprises a pore size of between 0.5 μm to 25 μm.

6. The stimulation electrode according to claim 3, wherein the porous tantalum oxide layer comprises a layer thickness of between 1 μm to 20 μm.

7. A method for producing a stimulation electrode comprising an electrically conducting base body, which encompasses tantalum,
on which a porous tantalum oxide layer is at least partially applied by means of high voltage pulses,
characterized in that a metallic protective layer is applied onto the porous tantalum oxide layer so as to prevent a hydrogen embrittlement of the porous tantalum oxide layer and such that the metallic protective layer is an outer layer of the base body adjacent tissue in which the electrode is implanted; and
wherein the tantalum oxide layer comprises an inner closed first oxide layer and an outer porous second oxide layer;
wherein the metallic protective layer comprises a layer thickness of between 0.01 μm to 10 μm; and
wherein the stimulation electrode and/or the porous tantalum oxide layer in combination with the metallic protective layer comprises an electric capacitance of at least 5 mF/cm$^2$.

8. The method according to claim 7, characterized in that the metallic protective layer is used up by means of at least one of the following methods: sputtering, spraying or evaporation.

* * * * *